United States Patent [19]

Schmehl

[11] Patent Number: 4,495,419
[45] Date of Patent: Jan. 22, 1985

[54] RADIATION DETECTION DEVICE

[76] Inventor: Stewart J. Schmehl, 241 Midland Ave., Montclair, N.J. 07042

[21] Appl. No.: 387,422

[22] Filed: Jun. 11, 1982

[51] Int. Cl.³ .......................... G01T 1/202; G01T 7/00
[52] U.S. Cl. ................................ 250/363 S; 250/505.1
[58] Field of Search ............ 250/363 R, 363 S, 505.1, 250/366 (U.S. only)

[56] References Cited

U.S. PATENT DOCUMENTS

| | | | |
|---|---|---|---|
| 3,011,057 | 11/1961 | Anger | 250/366 |
| 3,128,380 | 4/1964 | Nirschl | 250/366 |
| 3,263,079 | 7/1966 | Mertz et al. | 378/2 |
| 3,462,601 | 8/1969 | Sternglass | 250/369 |
| 3,562,528 | 2/1971 | Joyce | 250/366 |
| 3,633,478 | 1/1972 | Ishimatsu | 250/213 VT |
| 3,668,395 | 6/1972 | Walker | 250/363 R |
| 3,748,470 | 7/1973 | Barrett | 378/2 |
| 3,825,757 | 7/1974 | Barrett et al. | 378/2 |
| 3,831,031 | 8/1974 | Barrett et al. | 378/2 |
| 3,882,310 | 5/1975 | Barrett | 378/2 |
| 4,371,897 | 2/1983 | Kramer | 358/294 |

FOREIGN PATENT DOCUMENTS 560195 5/1977 U.S.S.R. .................. 250/363 S

Primary Examiner—Janice A. Howell
Assistant Examiner—Constantine Hannaher
Attorney, Agent, or Firm—Ronald G. Goebel

[57] ABSTRACT

A radiation detection device is provided which comprises a box-like housing having a radiation permeable window located in one side.

A scintillator is mounted in the housing; the scintillator comprising a first tube of radiation permeable material encasing a central core of scintillation material such as sodium iodide surrounded by a light reflective material, and a means for converting light signals into electric signals are connected with the scintillator.

A rotating collimator surrounds the scintillator including a second tube of radiation permeable material, a plurality of channel forming members comprised of a radiation impermeable material formed in groups around the second tube, a plurality of groups being located axially along the second tube, wherein each group of channel forming members define a plurality of radial channels capable of being directed toward the radiation permeable window during rotation.

6 Claims, 2 Drawing Figures

RADIATION DETECTION DEVICE

BACKGROUND OF THE INVENTION

This invention relates to scintillation devices used in the detection and presentation of radiation data particularly radiation emanating from a radio-isotope injected into a patient which collects in an organ of interest such as the heart.

A scintillation scanner is an imaging device that consists of a collimator which discriminates between desired and undesired radiation, a scintillator, which converts the radiation into visible light, a light amplifier system which converts the light produced in the scintillator to an electrical current, and an electronic display system such as a cathode ray tube. During use, the detector moves or "scans" the area under study in a rectilinear fashion. Only radiation from the patient that passes through the collimator and reaches the detector is displayed.

A scintillation camera consists of a collimator made of a plurality of parallel holes, a scintillator, an array of light amplifiers and an electronic display system. In use, the camera is positioned over the area of interest and the collimator in this case allows only the radiation traveling along the center lines of the holes to strike the scintillator. Each scintillation is detected by the array of light amplifiers. The differential current from each of the amplifiers is electronically analyzed and thus the position of the scintillation is determined and then displayed. Such a system is described in U.S. Pat. No. 3,011,057 to H. O. Anger.

Multi-purpose systems, such as those described above, used for diagnostic purposes which function by detecting the location and quantity of a radioactive compound absorbed in an organ of interest in living bodies, specifically the human heart, have in the past been large, externally supported, detector mechanisms. These large detectors have had the problem of being fixed in space with respect to their external supports, while the patient being studied is in motion due to the necessity of the patient having to be placed in a physically stressful situation such as exercising on a treadmill. Procedures such as strapping the patient to the detector have proven to be of little value since they affect the ability of the patient to function normally and the strapping fails to hold the patient solidly to the detector.

The present invention is a small, hand-held device which does not require external, rigid supports and can be used to ascertain a two dimensional display of the organ under investigation.

SUMMARY OF THE INVENTION

The present invention provides a radiation detection device useful as a scintillation camera small enough to be hand-held which comprises a housing having a radiation permeable window in one side thereof. Mounted inside the housing is a tubular or cylindrical scintillator comprised of an outer tube of radiation permeable material such as aluminum which encases an inner core of scintillation material such as sodium iodide preferably surrounded by a light reflective material such as aluminum oxide. The ends of the scintillator each have a glass window formed therein and communicating with the windows are photomultiplier tubes. A cylindrical collimator is rotatably mounted around the scintillator having means for rotating the collimator located in the housing. The collimator comprises an inner tube or cylinder which surrounds the outer tube of the scintillator and to which the rotating means is coupled. A plurality of channel forming members comprised of a radiation impermeable material are mounted over the inner tubular member arranged radially with respect to the inner tube and spaced apart equally to form a plurality of equally spaced axial rows of channels. A group of four channel forming members produces radial channels spaced 90° apart. As the collimator is rotated all channels in an axial row in their turn are directed toward the radiation permeable window. An outer support tube of radiation permeable material encloses all channel members of the collimator.

Radiation from an organ under inspection is directed toward the radiation permeable window. Radiation passes through the outer support tube and that which is not absorbed by the material making up the channel forming members is directed through the channels where it passes through the material of the inner tube of the rotating collimator, the outer tube of the scintillator, the light reflective material and is then absorbed by the scintillation material. At the point of absorption, visible light is produced which is reflected off the light reflective material surrounding the scintillation material and passes through the glass windows where it reaches the photomultiplier tubes and is converted to electrical signals in the form of current. These signals along with the output of the rotating means are processed in a computer and can be displayed as a two dimensional image on a cathode ray tube.

DETAILED DESCRIPTION OF THE PREFERRED EMBODIMENTS

Figure 1:
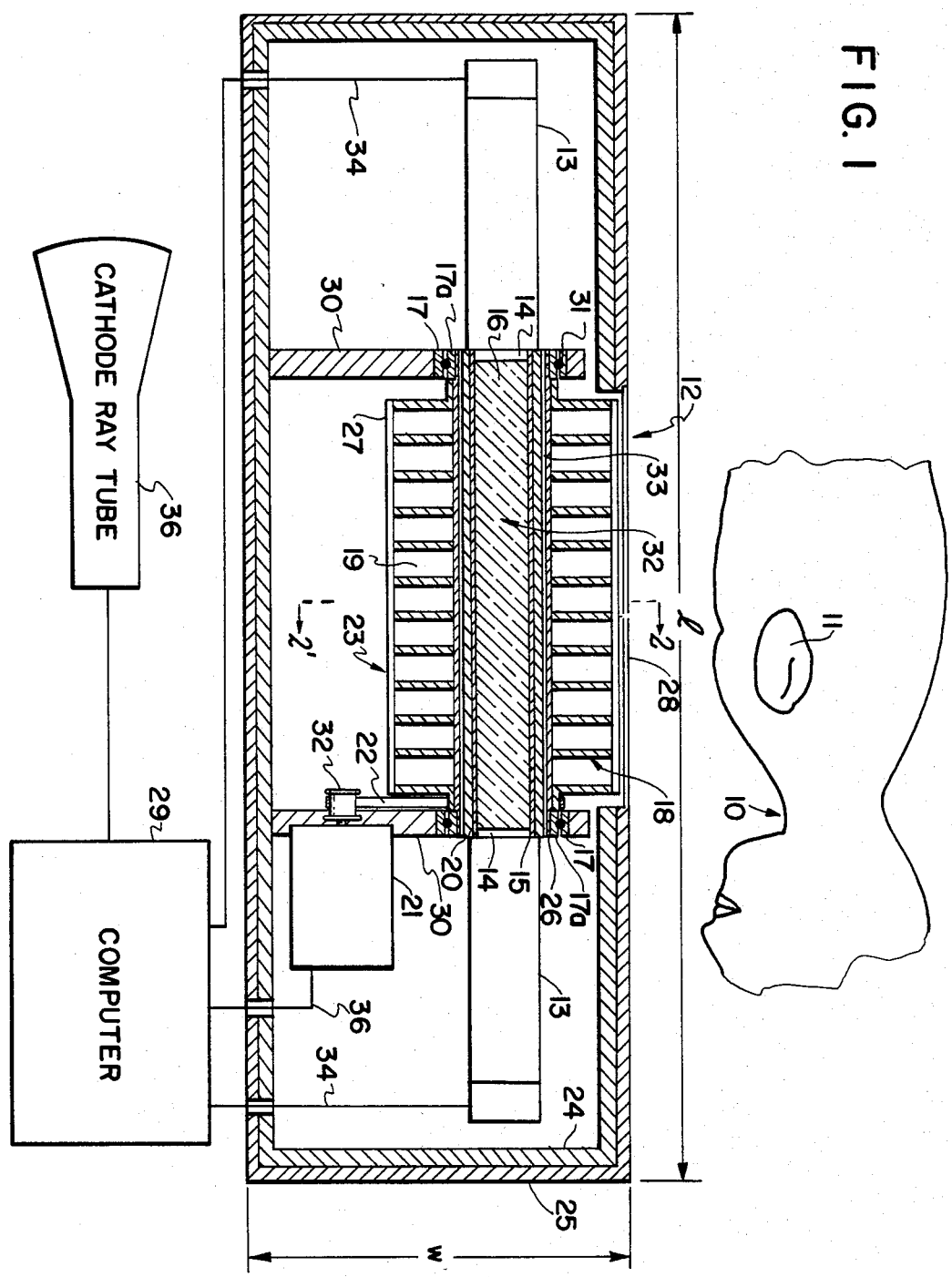
FIG. 1 is a sectional side view of the radiation detection device of the invention.

The drawings show a scintillation camera according to the invention indicated generally by 12 consisting of a metal box-like housing 25 having an aluminum radiation permeable window 28 formed on one side thereof and covered on all inside surfaces by an internal protective shield 24 made of a radiation impermeable material such as lead. The dimensions of the housing are as follows: length (l), 12 inches, width (w), 6 inches and height (h), 3 inches. These dimensions can be varied by those skilled in the art as necessary. However, the dimensions as described above allows the camera of the invention to be held by hand. A pair of bearing support brackets 30 are mounted on the inside of the housing at the long wall thereof opposite to the window-carrying wall and extend almost to such window-carrying wall spanning the window 28. The upper portion of each bracket has a circular aperture formed therein surrounded by an inner bearing surface 17.

A tubular or cylindrical collimator shown generally by 23 comprising an inner tube 26 made of a radiation permeable material having an outer bearing surface 17a at both ends is rotatably mounted in the circular aperture of the support brackets by means of ball bearings 31 which are nested between the inner and outer bearing surfaces of the brackets and inner tube, respectively. The tubular collimator is rotated by means of motor 21 having pulley 32 and belt 22 which passes around the tubular collimator adjacent to the right mounted bracket 30. The inner aluminum tube 26 of the collimator encloses an outer aluminum tube 20 of scintillator 32. A thin air space 33 lies between inner tube 26 and outer tube 20 so that the collimator is free to rotate about the scintillator 32. The scintillator consists of the outer aluminum tube containing in its central portion a sodium iodide crystal 16 surrounded by a reflective material 15 such as aluminum oxide. The ends of the outer tube 20 each have a glass window 14 formed therein. Mounted over the outside of inner aluminum tube 26 are a plurality of channel forming members 18 comprised of a radiation impermeable material such as lead arranged radially around the inner tube to form axial rows of channels 19. Each channel forming member consists of a pair of radial elements 18a and a support section 18b located therebetween. A group of four channel forming members is mounted circumferentially about outer aluminum tube 26 with adjacent members forming a radial channel 19 therebetween making a total of four channels spaced 90° apart and thus four rows of channels 19. Surrounding and enclosing the channel forming members is outer tubular support 27 made of radiation permeable material such as aluminum.

Mounted against each glass window 14 of the scintillator 32 is a photomultiplier tube 13. The output of each tube 34 is connected electronically to a computer 29 as is the output 36 of motor 21. The computer processes the electronic signals from the photomultiplier tubes and presents a display on cathode ray tube 36.

During use, without rotation of the collimator, a radioactive compound is injected into a patient 10. This compound collects in the organ of interest such as the heart 11. Radiation is emitted from the organ 11 towards the window 12. The radiation passes through the window 12, support housing 27 and impinges upon the collimator 23. Radiation which strikes the lead material of the collimator is absorbed. However, radiation which travels uninhibited through channels 19 passes through inner tube 26 and outer tube 20, the aluminum oxide 15 and is absorbed in sodium iodide crystal 16 at the core of the scintillator. At the point of absorption, visible light is produced by the scintillator. This light, through direct transmission or reflection off aluminum oxide 15, passes through glass window 14 and reaches photomultiplier tubes 13 where it is converted to an electrical current. Using electronic techniques, the position along the length of the crystal 16 of the radiation where it was absorbed may be determined. This technique is described in detail in U.S. Pat. No. 3,011,057 to H. O. Anger herein incorporated by reference. This positional information can be displayed on cathode ray tube 36 giving a one dimensional representation of organ 11.

Positional information, in a direction perpendicular to the one dimensional information described above, can be obtained by now rotating collimator 23 with motor 21. As one parallel row of channels 19 passes by window 21, information relating to its angular position is given by motor 21 to computer 26. Computer 26 then relates this angular information to the radiation positional information given by photomultiplier tubes 13. Thus by knowing where along the crystal 16 a particle was absorbed and at what angle the collimator holes 19 were pointing when the absorption took place, the computer can, using the proper algorithms, determine a two dimensional position for the radiation that was absorbed in crystal 16.

Figure 2:
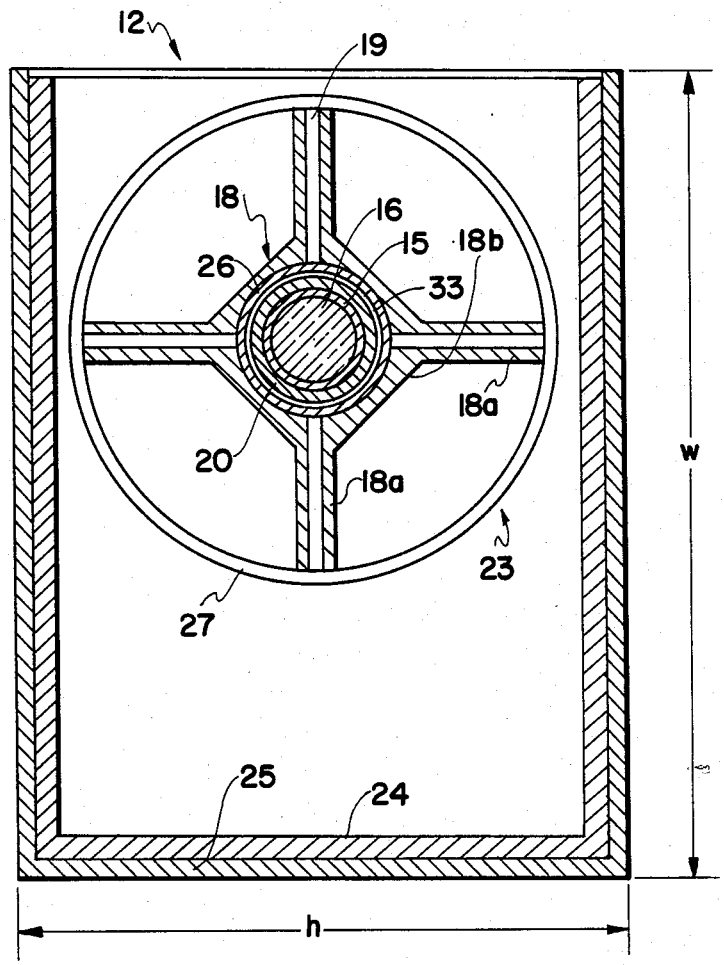
FIG. 2 is a sectional view of the radiation detection device of the invention through line 2—2' of FIG. 1.

The collimator shown in FIGS. 1 and 2 has been simplified for clarity. A typical collimator may have as many as 250 channels in each group of parallel channels each being 0.050 inches in diameter.

The present invention can be used with any type of scintillator material and the scintillator can be of any configuration. Also the present invention can be used with different types of display and storage systems both analog and digital. The photomultiplier tubes can also be replaced with other types of devices for converting light energy to electrical current and amplifiers such as solid state devices.

I claim:

1. A hand-held detection device comprising a housing having a radiation permeable window located therein and a rotating cylindrical collimator mounted in said housing, said collimator comprising a tubular member comprised of a radiation permeable material and a plurality of equally spaced radial rows of channels formed by channel forming members mounted on said tubular member, said collimator surrounding a tubular scintillator.

2. The detection device of claim 1 comprising means for rotating said collimator.

3. A hand held scintillation camera for determining a two-dimensional representation of the position of the source of radiation comprising:
    (a) a housing having a radiation permeable window located therein;
    (b) a tubular scintillator mounted in said housing, said scintillator comprising a first tube of radiation permeable material encasing a central core of scintillation material surrounded by a light reflective material, each end of said scintillator having a window formed therein;
    (c) means for converting a light signal into an electrical signal connected with said scintillator; and
    (d) a cylindrical collimator rotatably mounted in said housing and surrounding said scintillator comprising a second tube of radiation permeable material, a plurality of channel forming members comprised of a radiation impermeable material defining a plurality of equally spaced radial rows of channels capable of being directed toward said radiation permeable window during rotation;
    whereby radiation to be detected by the device passes through said radiation permeable window and through a row of said channels while said collimator is rotating and is absorbed by said scintillator where it is converted to visible light which is reflected by said light reflective material and passes through said means for converting and produces a two-dimensional representation of the position of the source of said radiation, said two-dimensional position being defined by a position along the axis of said tubular scintillator and a position perpendicular to the axis of said scintillator material obtained by said rotating collimator.

4. The device of claim 3 wherein said scintillation material is sodium iodide.

5. The device of claim 3 wherein said means for converting light signals into electrical signals is a photomultiplier tube.

6. A hand-held scintillation camera for determining a two-dimensional representation of the position of the source of radiation comprising:
    (a) a housing having a radiation permeable window located therein;

(b) a tubular scintillator mounted in said housing surrounded by an outer light reflective material, each end of said scintillator having a window formed therein;
(c) means for converting a light signal to an electrical signal communicating with each of said windows; and
(d) a cylindrical collimator rotatably mounted in said housing and surrounding said scintillator, said collimator having a plurality of equally spaced radial rows of channels;

whereby radiation to be detected by the device passes through said radiation permeable window and through a row of said channels while said collimator is rotating and is absorbed by said scintillator where it is converted to visible light which is reflected by said light reflective material and passes through said means for converting and produces a two-dimensional representation of the position of the source of said radiation, said two-dimensional position being defined by a position along the axis of said tubular scintillator material and a position perpendicular to the axis of said scintillator material obtained by said rotating collimator.

* * * * *